(12) United States Patent
Hofmann et al.

(10) Patent No.: US 7,171,264 B1
(45) Date of Patent: *Jan. 30, 2007

(54) INTRADERMAL DELIVERY OF ACTIVE AGENTS BY NEEDLE-FREE INJECTION AND ELECTROPORATION

(75) Inventors: Gunter A. Hofmann, San Diego, CA (US); Dietmar P. Rabussay, Solana Beach, CA (US); Lei Zhang, San Diego, CA (US)

(73) Assignee: Genetronics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/339,708

(22) Filed: Jan. 8, 2003

Related U.S. Application Data

(63) Continuation-in-part of application No. 09/567,404, filed on May 8, 2000, now Pat. No. 6,520,950.

(60) Provisional application No. 60/133,265, filed on May 10, 1999.

(51) Int. Cl.
*A61N 1/30* (2006.01)

(52) U.S. Cl. ...................................... 604/20

(58) Field of Classification Search ............... 604/503, 604/50, 501, 20, 71; 435/455
See application file for complete search history.

(56) References Cited

U.S. PATENT DOCUMENTS

| | | | | |
|---|---|---|---|---|
| 4,752,285 A | * | 6/1988 | Petelenz et al. ............... 604/20 |
| 5,013,293 A | * | 5/1991 | Sibalis .......................... 604/20 |
| 5,019,034 A | * | 5/1991 | Weaver et al. ................ 604/20 |
| 5,505,697 A | * | 4/1996 | McKinnon et al. ........... 604/71 |
| 5,667,491 A | * | 9/1997 | Pliquett et al. ............. 604/501 |
| 5,857,992 A | * | 1/1999 | Haak et al. .................... 604/20 |
| 5,993,434 A | * | 11/1999 | Dev et al. .................... 604/501 |
| 6,035,234 A | * | 3/2000 | Riddle et al. ................. 604/20 |
| 6,148,232 A | * | 11/2000 | Avrahami ..................... 604/20 |
| 6,520,950 B1 | * | 2/2003 | Hofmann et al. ........... 604/503 |
| 2002/0102729 A1 | * | 8/2002 | MacLaughlin et al. ..... 435/455 |

* cited by examiner

*Primary Examiner*—Manuel Mendez
(74) *Attorney, Agent, or Firm*—Daniel M. Chambers; Douglas C. Murdock; BioTechnology Law Group

(57) ABSTRACT

Methods are proved for introducing a biologically active agent into cells of a subject by introducing the agent in a form suitable for electrotransport into a region of tissue of the subject using one or more needle-free injectors, and applying a pulsed electric field to the region of tissue, thereby causing electroporation of the region of tissue. The combination of needle-free injection and electroporation is sufficient to introduce the agent into cells in skin, muscle or mucosa. For example, the region of tissue can be contacted with two oppositely charged injectors, one acting as the donor electrode and one acting as the counter electrode, or a single injector and one or more electrodes can be used. In addition, needle-free injection may be used in combination with suitable non-invasive electrode configurations. The active agents delivered into cells using the invention method can be small molecules, polynucleotides, polypeptides, and the like.

107 Claims, 5 Drawing Sheets

- ■ 1. b.j. DNA
- ▲ 2. b.j. DNA + EP
- ▼ 3. i.d. DNA
- ● 4. i.d. DNA + EP
- ● 5. b.j. subunit
- □ 6. i.m. subunit

INTRADERMAL DELIVERY OF ACTIVE AGENTS BY NEEDLE-FREE INJECTION AND ELECTROPORATION

RELATED APPLICATION

This application is a Continuation-In-Part application of U.S. Ser. No. 09/567,404, filed May 8, 2000, now U.S. Pat. No. 6,520,950 which relies for priority under 35 U.S.C. § 119(e), upon U.S. Provisional Application Ser. No. 60/133,265, filed May 10, 1999, each of which is incorporated herein by reference in its entirety.

TECHNICAL FIELD

This invention generally relates to methods for delivery of an active agent to a subject and more specifically to the use of electroporation and needle-free delivery of an active agent to a subject.

BACKGROUND

A cell has a natural resistance to the passage of molecules through its membranes into the cell cytoplasm. Scientists in the 1970's first discovered "electroporation," the use of electrical fields to create pores in cells without causing permanent damage to the cells. This discovery made possible the insertion of large molecules directly into cell cytoplasm. Electroporation was further developed to aid in the insertion of various molecules into cell cytoplasm by temporarily creating pores in the cells through which the molecules pass into the cell.

Electroporation has been used in both in vitro and in vivo procedures to introduce foreign material into living cells. With in vitro applications, a sample of live cells is first mixed with the agent to be introduced therein and placed between electrodes, such as parallel plates. Then, the electrodes are used to apply an electrical field to the mixture containing the cells and the agent to be introduced therein.

With in vivo applications of electroporation, electrodes are provided in various configurations such as, for example, a caliper that grips the epidermis overlying a region of cells to be treated. Alternatively, needle-shaped electrodes may be inserted into the patient, to access more deeply located cells. In either case, before, simultaneously, or after the agent is injected into the treatment region, the electrodes are used to apply an electrical field to the region. See, for example, U.S. Pat. No. 5,019,034, issued May 28, 1991 and U.S. Pat. No. 5,702,359, issued Dec. 30, 1997.

Electroporation (both in vitro and in vivo) functions by causing cell membranes to which a brief high voltage pulse is administered to temporarily become porous, whereupon molecules can enter the cells. In some electroporation applications, the electric field comprises a single square wave pulse on the order of 1000 V/cm, of about 100 microseconds duration. Such a pulse may be generated, for example, in known applications of the ElectroSquarePorator T820, made by the BTX Division of Genetronics, Inc.

Electroporation has been recently suggested as an alternate approach to the treatment of certain diseases such as cancer by introducing a chemotherapeutic drug directly into the cell. For example, in the treatment of certain types of cancer with chemotherapy it is necessary to use a high enough dose of a drug to kill the cancer cells without killing an unacceptably high number of normal cells. If the chemotherapy drug could be inserted directly inside the cancer cells, this objective could be achieved. However, some of the best anti-cancer drugs, for example, bleomycin, cannot penetrate the membranes of certain cancer cells effectively under normal circumstances. To overcome this difficulty, electroporation has been used to cause bleomycin to penetrate the membranes of cancer cells.

Electroporation-assisted chemotherapy typically is carried out by injecting an anticancer drug directly into the tumor and applying an electric field to the tissue between a pair of electrodes. The field strength must be adjusted reasonably accurately so that electroporation of tumor cells occurs without damage, or at least with minimal damage, to any normal or healthy cells. Typically, this method is employed with tumors located on the exterior of the patient's body by applying electrodes to the body surface on opposite sides of the tumor, thus creating an electric field between the electrodes. When the field is uniform, the distance between the electrodes can then be measured and a suitable voltage, derived according to the formula $E=V/d$ (wherein E=electric field strength in V/cm; V=voltage in Volts; and d=distance in cm), can then be applied to the electrodes. However, when the tumors to be treated are large, irregular in shape, or located within the body interior, it is more difficult to properly locate electrodes and measure the distance between them so as to accurately calculate the voltage that is to be applied. In such cases, needle array electrodes as, for example, described in U.S. Pat. No. 5,993,434 (Dev and Hofmann) have proven to be advantageous.

Using these and related techniques (for example, the molecule can be delivered encapsulated in a liposome), electroporation has been used to deliver molecules into many different types of cells. For example, electroporation has been used to deliver biologically active agents to various human and mammalian cells, such as egg cells (i.e., oocytes), sperm, platelets, muscle, liver, skin, and red blood cells. In addition, electroporation has been used to deliver molecules to plant protoplasts, plant pollen, bacteria, fungi, and yeast. A variety of different biologically active molecules and agents have been delivered to cells using this technique, including DNA, RNA and various chemical agents.

Vaccination is the most cost-effective way to prevent disease. However, there are still many diseases for which no vaccine exists or for which the currently available vaccines are inadequate. DNA immunizations, which entail the administration of DNA encoding an antigen, may offer solutions in at least some of these cases. Moreover, DNA vaccines offer the use of host cells as bioreactors for the production of proteins in vivo (Tang, D. C., et al., (1992) *Nature* 356:152–4). By doing so, DNA vaccines mimic a viral infection, improve antigen presentation to the immune system relative to standard protein vaccines, and work more effectively as a result (Ulmer, J. B., et al., (1993) *Science* 259:1745–9). Moreover, DNA vaccines offer these potential benefits without many of the safety and stability concerns associated with the administration of infectious agents.

DNA immunization has been effective in several small animal models (Donnelly, J. J., et al., (1997) Annu. Rev. Immunol. 15:617–48). However, demonstrating its effectiveness has been much more challenging in larger animals and humans. Numerous studies have shown that the greatest power of DNA vaccines may be their ability to prime the immune system for responses to other vaccines (Richmond, J. F., et al., (1998) *J. Virol.* 72:9092–100; Robinson, H. L., et al., (1999) *Nat. Med.* 5:526–34).

The first hypodermic syringe was developed by a French surgeon, Charles-Gabriel Pravaz, in 1853 to take advantage of the highly permeable interstitial tissue below the skin surface to transport pharmaceuticals to active sites. Although there have been developments in hypodermic syringes since then, the technology has remained essentially unchanged for the past 150 years. Needle-free injection was developed when workers on hydraulic equipment noticed that high-pressure squirts of hydraulic oil would pierce the skin. The first description of needle-free injection was in Marshall Lockhart's 1936 patent for "jet injection." Then, in the early 1940's Higson and others developed high-pressure "guns" using a very fine jet of liquid medicament to pierce the skin and deposit it into the tissue underneath. In World War II, needle-free guns were used extensively to inoculate troops en masse against infectious disease. Later, needle-free guns were applied more generally in large-scale vaccination programs.

However, these early needle-free injectors were used on multiple patients and fears about the transmission of hepatitis B and HIV infection by reuse of the injectors led to a sharp decline in their use. Until recently, the main application of such devices was veterinary, with a few being used by diabetics for self-treatment.

In the past 50 years, over 300 patents have been filed in the needle-free delivery area. Although various improved products have come to the market, none has gained wide use and remnants of the older devices remain to this day. These devices tend to be expensive to purchase and difficult to use, requiring the user to perform a series of complicated steps to set up the device for use. For example, some of these systems require the user to fit a needle to the delivery device temporarily in order to draw liquid containing the desired active agent into the device from a vial. Therefore, even the more modern needle-free delivery systems do not address the needs of the market for an easy to use, low cost, and simple system. Consequently, needle-free delivery has not come into widespread use.

Despite this apparent failure of needle-free delivery, the pharmacokinetics and pharmacodynamics of needle-free delivery are well documented. Accelerating a jet of liquid to high speed provides power for the liquid to penetrate the stratum corneum as well as individual cell membranes. Thus, there is a need in the art for new and better methods for transporting molecules, such as biologically active agents, across the stratum corneum and/or cell membranes in treatment of a variety of conditions and diseases.

SUMMARY OF THE INVENTION

The present invention overcomes such problems in the art by providing methods for introducing biologically active agents into cells without use of a hypodermic needle. In one embodiment according to the present invention, a biologically active agent is introduced in a form suitable for direct or indirect electrotransport into a region of tissue of the subject using one or more needle-free injectors, and an electric field is applied to the region of tissue, thereby causing electroporation of the region of tissue prior to, simultaneously with, and/or subsequently to introducing the agent. Direct electrotransport refers to the transport of molecules subjected to an electrical or magnetic force, indirect electrotransport refers to the transport of molecules facilitated by electric forces which act primarily on transport barriers, e.g., cell membranes, which become more permeable as a result of electric forces. The combination of needle-free injection and electroporation is sufficient to introduce the active agent into the cell and allows for delivery of pharmaceutical compounds, nucleic acid constructs, or other agents into cells contained within the tissue region so treated.

In another embodiment according to the present invention, a biologically active agent is introduced into cells in a region of tissue of a subject by contacting the region of tissue or adjacent tissue with two or more spaced apart needle-free injectors while injecting a biologically active agent into the tissue, and applying an electrical field to the tissue via the two or more injectors prior to, simultaneously with, and/or subsequently to injection of the agent so as to electroporate the region of tissue, whereby the combination of needle-free injection and electroporation is sufficient to introduce the agent into the cell.

In yet another embodiment according to the present invention, a biologically active agent is introduced into cells in a region of tissue of a subject by contacting the region of tissue with at least one needle-free injector while injecting an agent suitable for direct or indirect electrotransport into the region of tissue, and applying an electrical field across the region of tissue using the at least one injector prior to, simultaneously with, and/or subsequently to injection of the agent, whereby the combination of needle-free injection and electroporation is sufficient to introduce the agent into the cell.

BRIEF DESCRIPTION OF THE DRAWINGS

In FIG. 1A, two needle-free injectors are disposed in spaced apart relation to one another and in contact with the surface of a region of tissue of the subject. The oppositely charged injectors act as electrodes for conducting electroporation, being connected with an electrical source, such as a pulse generator, such that an electrical current is delivered through the region of tissue by completing the circuit between the two electrically conducting injector tips. One injector is the active or donor electrode and the second, oppositely charged, injector is the counter or return electrode.

DETAILED DESCRIPTION OF THE INVENTION

Figure 1A:
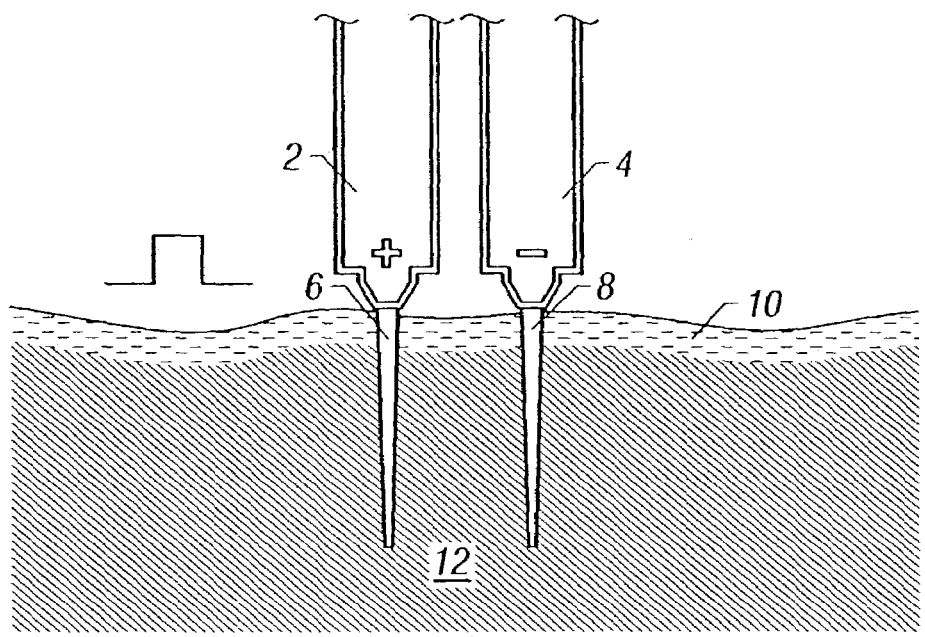
FIGS. 1A and B show diagrams illustrating the invention method wherein electrically conducting needle-free injectors are used as the electrodes for delivering an electrical impulse to a region of tissue.

According to the present invention, there are provided methods for introducing a biologically active agent into cells in a region of tissue of a subject by injecting the agent in a form suitable for direct or indirect electrotransport into a region of tissue of the subject using one or more needle-free injectors, and applying an electric field to the region of tissue, thereby causing electroporation of the region of tissue prior to, simultaneously with, and/or subsequently to injection of the agent. The combination of needle-free injection and electroporation is sufficient to introduce the agent into the cell.

A "needle-free injector," as the term is used herein, refers to a device that injects an agent into tissue without the use of a needle, for example as a small stream or jet, with such force (usually provided by expansion of a compressed gas, such as carbon dioxide through a micro-orifice within a fraction of a second) that the agent pierces the surface of the tissue and enters underlying tissue and/or muscle. In one embodiment, the injector creates a very high-speed jet of liquid that painlessly pierces the tissue. Such needle-free injectors are commercially available and can be used by those having ordinary skill in the art to introduce agents (i.e. by injection) into tissues of a subject. Examples of needle-free injectors that can be utilized in practice of the invention methods include those described in U.S. Pat. Nos. 3,805,783; 4,447,223; 5,505,697; and 4,342,310.

As used herein, the term "introduce," "inject" or "injecting," and grammatical equivalents thereof, as applied to the action of a needle-free injector means that the agent is forced through at least the surface of the tissue (e.g., the mucosa or epidermis, stratum corneum, or dermis of skin) and, preferably, delivered into underlying tissue and/or musculature using a needle-free injector as described herein.

A desired agent in a form suitable for direct or indirect electrotransport is introduced (e.g., injected) using a needle-free injector into the tissue to be treated, usually by contacting the tissue surface with the injector so as to actuate delivery of a jet of the agent, with sufficient force to cause penetration of the agent into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver active agents to all types of tissues, particularly to skin and mucosa. In some embodiments, a needle-free injector may be used to propel a liquid that contains DNA molecules or a drug toward the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

In addition to their function in introducing the active agent, two or more needle-free injectors can also be used to apply an electric field to the tissue for electroporation of cell membranes therein. As shown in FIG. 1A, two needle-free injectors 2 and 4, each project a jet of liquid 6 and 8 containing the biologically active agent. The injectors are disposed in spaced relation to one another and in close contact with the surface 10 of a region of tissue 12 of the subject. The portion of the injectors in contact with the tissue surface are electrically conductive and are in electrical connection with an electrical source (not shown), such as a pulse generator, such that electroporation is accomplished by delivering an electrical current through the region of tissue by completing the circuit between the two electrically conducting injector tips. As shown in FIG. 1A, injector 2 is the active or donor electrode and injector 4 is the counter or return electrode. In other embodiments, both injectors can act as donor electrodes. Usually, although not always, the injectors are also in contact with the tissue surface while the active agent is introduced.

Figure 1B:
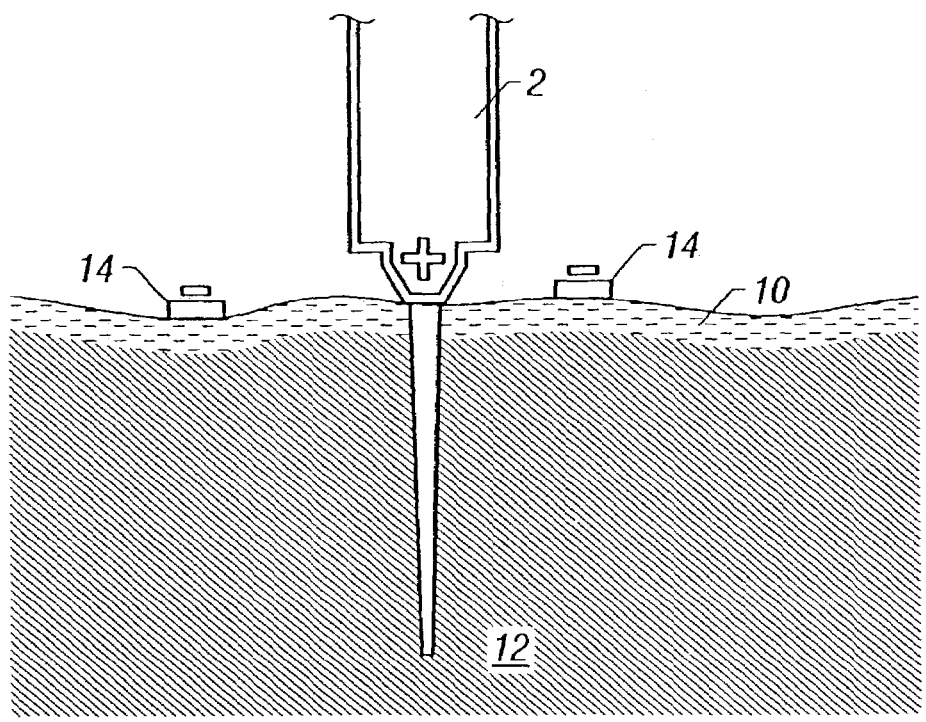
In FIG. 1B, one needle-free injector contacts the surface of a region of tissue while providing an electrical current in conjunction with two oppositely charged electrodes. The injector acts as the active or donor electrode and the two ring electrodes act as counter or return electrodes.

Another embodiment of the invention method wherein the injector is utilized to apply an electrical field to the surface of a subject is shown in FIG. 1B. In this embodiment of the invention method, at least one injector contacts the surface of the tissue and provides an electrical current in conjunction with one or more electrodes, such as, for example, a ring electrode(s). As shown in FIG. 1B, injector 2 contacts surface 10 of a region of tissue 12 so as to act as the active or donor electrode while charged ring electrode 14 acts as the counter or return electrode.

Figure 2A:
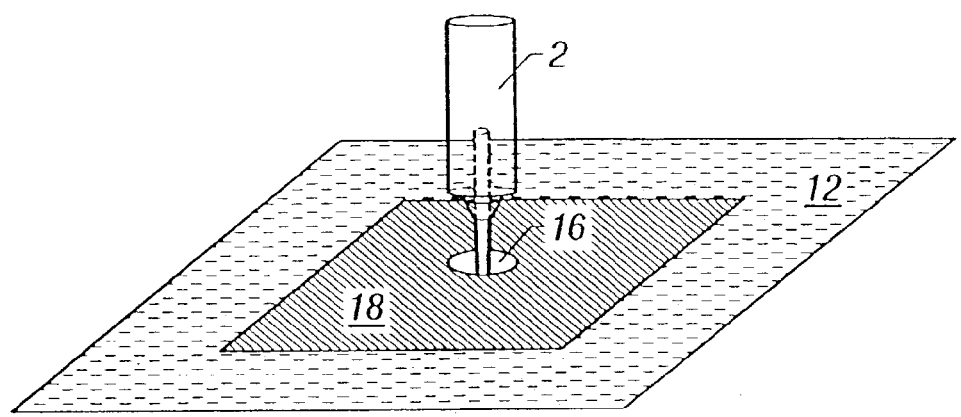
FIG. 2A is a schematic drawing showing a needle-free injector that is not in contact with the skin injecting a liquid into tissue through an opening in an array electrode containing multiple positive and negative electrodes.
Figure 2B:
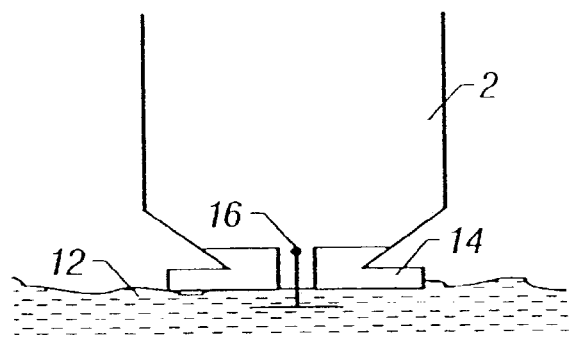
FIG. 2B is a schematic drawing showing a needle-free injector with array electrode attached to the nozzle area and an opening in the array electrode allowing the liquid jet to go through the electrode into the skin.
Figure 2C:
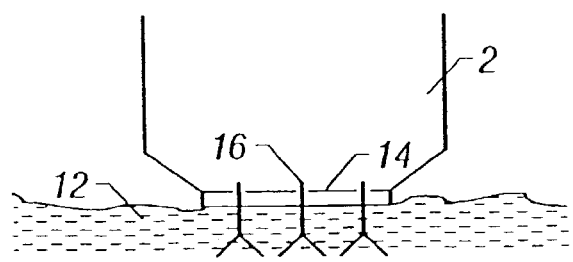
FIG. 2C is a schematic drawing showing a needle-free injector with an array electrode attached to the nozzle area. The array electrode has multiple openings to allow multiple liquid jets to pass through the array electrode into the skin.

In yet another embodiment shown in FIG. 2, the needle-free injector introduces a conductive fluid as a jet through an opening 16 in an array electrode 18, which contains multiple positive and negative electrodes. e.g., a micropatch electrode as described in U.S. patent application Ser. No. 09/134,245, filed on Aug. 14, 1998, which is hereby incorporated herein in its entirety by reference). By example, the electrode can be a meander electrode that consists of an array of interweaving electrode fingers with alternating polarity. The width of individual electrodes about 2 mm and the gap between electrodes is about 0.2 mm. Alternatively, the electrode can be made of a porous material such that e.g., polyacrylamide hydrogels the liquid jet from the injector passes through the pores of the electrode to the target layers of the tissue.

Various shapes and compositions of the needle-free injector tip that delivers the electric pulse (or electrode, if used) can be used so long as it is capable of delivering a sufficient electric pulse as set forth herein. Optionally, at least the portion of the needle-free injector that is pressed against the tissue in practice of the invention methods is insulated to protect against excess heat or burning, current leakage, shock, etc. Appropriate electric pulsing parameters are set forth herein or can be determined using the teachings herein and, in view of these parameters, the skilled artisan can select among various suitable materials (e.g., ceramic, metal, etc.) and configurations (ring, solid disc, etc.) for manufacture of the portion of the needle-free injector (and electrodes, if used) that contact the tissue to be electroporated.

In addition, to the injectors, optional electrodes, and electrical source, the apparatus used in practice of the invention method typically further includes a means for controlling the amount of current passing from the device and through the contacted surface, as well as additional control elements typical of electroporation systems as are known in the art.

The liquid jets themselves from the injector(s) can be made highly electrically conductive by using a conductive suspension or solution of the agent, e.g., in an ionic solution, such as a saline solution. As used herein, the term "conductive" means that the fluid has a specific resistivity sufficient to allow the application of an effective electrical field without unacceptable heating of the liquid jet occurring during that electrical pulse. The jets of conductive fluid then can act, not only as liquid needles, but also as electrodes. Thus, when conductive jets of liquid are introduced into tissue, the injector device does not need to touch the tissue into which the active agent is introduced. Rather, the injector can be placed in proximity to the surface of the tissue and the conductive jet from a needle-free injector device in combination with such another jet, or in combination with one or more surface electrodes is sufficient to complete the electrical circuit through the tissue. As one of skill in the art will appreciate, therefore, in the invention methods the active agent can be introduced either as a jet of conductive fluid from a needle-free injector (without touching the surface of the tissue with an electrically conductive injector device), or a low conductivity jet of fluid can be introduced while contacting the tissue surface with an electrically conductive injector device in any of the combinations of injector(s) and electrode(s) described herein.

Typically in this situation, the electroporation pulse would be administered "substantially contemporaneously" with the injection of the agent into the tissue. As used herein, the term "substantially contemporaneously" can mean that the electroporation pulse is delivered during the time that the jet remains intact (i.e., has not broken up). For example, the electroporation pulse can be timed, (e.g., mechanically or electronically) to coincide with the jet driving mechanism in the injector. If electrodes are placed on the surface of the tissue for the purpose of promoting current flow (see FIG. 1B for example), timing sensors can be incorporated into the electrodes to coordinate the electroporation pulse and the jet driving mechanism. Alternatively, the term "substantially contemporaneously" can mean that the needle-free injector is activated to inject the agent and the electric pulse is applied to the region of skin or mucosa to be treated reasonably close together in time. Alternatively, an electrical current can be provided before or following introduction of a therapeutic agent to the tissue of the subject. When multiple electrical impulses are applied, the agent can be administered in a form suitable for direct or indirect electrotransport before or after each of the pulses, or at any time between the electrical pulses.

The active agent can include ionic species, molecules having charged functionalities, or molecules of neutral charge. The agent may be completely charged (i.e., 100% ionized), completely uncharged, or partly charged and partly uncharged. Alternatively, two or more agents of differing charge (or % ionization) can be combined to arrive at a desired level of charge for the combination, or an uncharged active agent can be contained in a medium suitable for direct or indirect electrotransport, such as a charged liquid (e.g., a solvent). Various degrees of ionization of the medium containing the active agent can be employed to produce the agent in a form suitable for electrotransport. For example, the liquid medium containing the active agent can be ionized from about 5% to about 95% by volume, or the liquid medium can be ionized from about 10% to about 75%, or from about 30% to about 50% by volume.

Electroporation as utilized in the invention method is a method of increasing the permeability of tissue and cell membranes which allows transport, or migration, of an agent through tissue or across cell membranes into cells. For example, electroporation can include applying a voltage across tissue to increase the permeability of the tissue and at least a portion of the cell membranes of cells in the tissue. If the tissue is in the presence of an agent in a form suitable for electrotransport, as described herein, the agent migrates across the tissue and into cells of the tissue.

The electric field applied in practice of the invention method is determined by the nature of the tissue, the size of the selected tissue, and its location. It is desirable that the field be as homogeneous as possible and of the correct amplitude. Excessive field strength results in lysing of cells, whereas a low field strength results in reduced efficacy. When the region of tissue being treated is skin or mucosa, during electroporation a voltage sufficient to cause that region of the epidermis to become electroporated is applied to the portion of the epidermis or tissue into which the active agent is introduced.

The electric pulse can be provided by any electronic device or electric pulse generator that provides an appropriate electric pulse sufficient for introducing an active agent (e.g., a therapeutic agent) in a form suitable for direct or indirect electrotransport into target cells. The waveform of the electrical signal provided by the pulse generator during electroporation can be an exponentially decaying pulse, a square pulse, a unipolar oscillating pulse train, or a bipolar oscillating pulse train, or any combination of these forms. The nominal electric field strength can be from about 10 V/cm to about 20 kV/cm. The nominal electric field strength is determined by computing the voltage between any two injectors (injector and one or more electrodes) divided by the distance between the injectors (or injector and one or more electrodes). The pulse length is generally in the range from about ten µs to 100 ms. There can be any desired number of pulses, typically one to about 100 pulses per second. The interval between pulse sets can be any suitable time, such as one second. The waveform, electric field strength and pulse duration may also depend upon the type of cells or tissue and the type of agents that are to enter the cells during electroporation.

Each pulse wave form has particular advantages; square wave form pulses provide increased efficiencies in transporting compounds into the cells in comparison to exponential decay wave form pulses, and the ease of optimization over a broad range of voltages, as described, for example, in Saunders, *Guide to Electroporation and Electrofusion,* 1991, pp 227–47. Preferably the waveform used is an exponential or a square wave pulse. Other wave forms such as rectangular or triangular will be known in the art and are included herein.

The electric fields needed for in vivo cell electroporation of various cell types are generally similar in magnitude to the fields required for cells in vitro and are well known in the art. Presently preferred magnitudes are in the range of from 10 V/cm to about 1300 V/cm. The higher end of this range, over about 600 V/cm, has been verified by in vivo experiments of others reported in scientific publications.

The nominal electric fields can be designated either "high" or "low." It is presently preferred that, when high voltage fields are used, the nominal electric field is from about 700 V/cm to 1300 V/cm and more preferably from about 1000 V/cm to 1300 V/cm. It is presently preferred that, when low fields are used, the nominal electric field is from about 10 V/cm to 200 V/cm, and more preferably from about 25 V/cm to 75 V/cm.

In a particular embodiment of the present invention, it is presently preferred that when the electric field is low, the pulse length is long, i.e., the "low voltage long pulse" mode of electroporation. For example, when the nominal electric field is about 25 V/cm to 75 V/cm, it is preferred that the pulse length is about 1 to 80 msec. For this type of low voltage long pulse electroporation, a square wave pulse is preferably used. Square wave electroporation systems deliver controlled electric pulses that rise quickly to a set voltage, stay at that level for a set length of time (pulse length), and then quickly drop to zero. Square wave electroporation pulses have a gentler effect on the cells than an exponential decay pulse, and therefore, yield higher cell viability and better transformation efficiency for the electroporation of plant and mammalian tissues. Exemplary pulse generators capable of generating a square pulsed electric field include, for example, the ElectroSquarePorator (T820) pulse generator (BTX division of Genetronics, Inc., San Diego, Calif.), which can generate a square wave form of up to 3000 volts and a pulse length from about 5 μsec to about 99 msec. The T820 ElectroSquarePorator is active in both the High Voltage Mode (HVM) (100–3000 Volts) and the Low Voltage Mode (LVM) (10–500 Volts). The pulse length for LVM is about 0.3 msec to 99 msec and for HVM, about 5 μsec to 99 μsec, with multiple pulsing capability from about 1 pulse to 99 pulses. Additional electroporation apparatus are commercially available and can be used in practice of the invention methods, for example, the ECM600 (BTX division, Genetronics, Inc.), which can generate an exponential wave form.

Although electroporation of the region of tissue treated can be prior to, simultaneously with, and/or subsequently to injection of the agent, the chemical composition of the agent will dictate the most appropriate time to administer the agent in relation to the administration of the electric pulse for electroporation. For example, while not wanting to be bound by a particular theory, it is believed that a drug having a low isoelectric point (e.g., neocarcinostatin, IEP=3.78), would likely be more effective if administered post-electroporation in order to avoid electrostatic interaction of the highly charged drug within the field. Another group of drugs (such as bleomycin) has a very negative log P, (P being the partition coefficient between octanol and water), are very large in size (MW about 1400), and/or are hydrophilic, thereby associating closely with the lipid membrane. Such drugs diffuse very slowly into a tumor cell. Therefore, in practice of the invention method, drugs having such characteristics are typically administered prior to or substantially simultaneously with the electric pulse.

In addition, certain biologically active agents may require chemical modification in order to facilitate more efficient entry into the cells and/or electrotransport. For example, an agent with poor water solubility, such as taxol, can be chemically modified using methods known in the art, to increase solubility in water.

The agent (and medium) may undergo electrotransport through pores created in cell membranes (e.g., during electroporation) by electromigration, electroosmosis, or a combination of the two. (Electroosmosis has also been referred to as electrohydrokinesis, electro-convection, and electrically-induced osmosis.) In general, electroosmosis of a therapeutic species into a tissue results from the migration of a liquid in a non-conducting capillary system in which the species is contained, as a result of the application of electromotive force to the therapeutic species reservoir., i.e., solvent flow induced by electromigration of other ionic species (C. Morris and P. Morris, *Separation Methods in Biochemistry*, New York Interscience Publishers, Great Britain, 1964, pp 632, 639).

In conjunction with any of the above-described procedures, a brief period of iontophoresis may optionally be applied to distribute the agent between the electrodes (e.g., the injectors) before, during, or after pulsing for electroporation. Iontophoresis is a process that can be used to transport molecules across tissue without necessarily causing electroporation, especially once enhanced electroporation has occurred. For iontophoresis, an electrical potential of much lower voltage and greater duration than is used for electroporation is applied to the region of tissue treated. For example, electroporation of the stratum corneum is caused by large pulses (between about 50 volts and about 500 volts at the electrodes), while iontophoresis is often caused by application of essentially steady (direct current), relatively small voltages (between about 0.1 Volt and about 5 Volt) or currents, which transport molecules through pre-existing pathways (see, for example, B. H. Sage, "Iontophoresis" in *Percutaneous Penetration Enhancers* E. W. Smith and H. I. Maibach, Eds., CRC Press, pp. 351–368, 1995). Therefore, in one embodiment, iontophoresis through skin tissue is practiced in conjunction with the invention methods by maintaining a constant current of about 1 mA for 30 seconds. Those of skill in the art will know how to select appropriate parameters to be used for iontophoresis of other types of tissues.

During iontophoresis, ions present in a sustained low voltage field will migrate toward sources of opposite charge. Thus, an active agent having at least some percent ionization will migrate towards an oppositely charged electrode through an electroporated membrane into subcutaneous, interstitial fluids. Neutral molecules can also be moved via iontophoresis by repeated contact of charged particles moving in one direction, such that net transport of the neutral molecular species occurs because of the transport of the electrically charged species. Iontophoresis is most efficient when the low voltage field for the iontophoresis is temporarily interrupted when the pores have retracted to a size at which the transport rate drops below a selected level (or is maintained) while a new electrical pulse having the characteristics to induce electroporation is applied.

During iontophoresis, the skin resistance changes much more slowly, and in lesser magnitude than during electroporation, and this skin resistance behavior is believed to be due to changes of ionic composition of solutions within pre-existing aqueous pathways (see, for example, S. M. Dinh, C-W. Luo and B. Berner "Upper and Lower Limits of Human Skin Electrical Resistance in Iontophoresis" *AIChe J.* 39:2011–2018, 1993). Thus, the larger skin resistance during iontophoresis means that the electric field is more confined to the surface of the tissue than during electroporation.

The term "iontophoresis" as used herein refers to (1) the delivery or transport of charged drugs or agents by electromigration, (2) the transport and/or delivery of uncharged drugs or agents by the process of electroosmosis, (3) the transport and/or delivery of charged drugs or agents by the combined processes of electromigration and electroosmosis, and/or (4) the transport and/or delivery of a mixture of charged and uncharged drugs or agents by the combined processes of electromigration and electroosmosis.

During the electrotransport process certain modifications or alterations of the skin or mucosal tissue may occur, such as increased ionic content, hydration, dielectric breakdown, extraction of endogenous substances, and electroporation. Any electrically assisted transport of species enhanced by modifications or alterations to a body surface (e.g., formation of pores in the skin) are also included in the term electrotransport as used herein.

The biologically active agents and active agents introduced according to the invention methods include drugs (e.g., chemotherapeutic agents), nucleic acids (e.g., polynucleotides), peptides and polypeptides, including antibodies and other molecules for delivery to a subject. For example, the polypeptide can be an antigen introduced for the purpose of raising an immune response in the subject into whose cells it is introduced. Alternatively, the polypeptide can be a hormone, such as calcitonin, parathyroid hormone, erythropoietin, insulin, a cytokine, a lymphokine, a growth hormone, a growth factor, and the like, or a combination of any two or more thereof. Additional illustrative polypeptides that can be introduced into cells using the invention method include blood coagulation factors and lymphokines, such as tumor necrosis factor, interleukins 1, 2 and 3, lymphotoxin, macrophage activating factor, migration inhibition factor, colony stimulating factor, $\chi$-interferon, $\beta$-interferon, $\chi$-interferon (and subtypes thereof), and the like.

Polynucleotides or oligonucleotides that can be introduced according to the invention methods include DNA, cDNA, and RNA sequences of all types. For example, the DNA can be double stranded DNA, single-stranded DNA, complexed DNA, encapsulated DNA, naked RNA, encapsulated RNA, and combinations thereof. Such agents are introduced by needle-free injection and electroporation as described herein in an amount to modulate cell proliferation or to elicit an immune response, either against the nucleic acid or a protein product encoded by the nucleic acid.

The polynucleotides can also be DNA constructs, such as expression vectors, expression vectors encoding a desired gene product (e.g., a gene product homologous or heterologous to the subject into which it is to be introduced), and the like. A therapeutic polypeptide (one encoding a therapeutic gene product) may be operably linked with a regulatory sequence such that the cells of the subject are transfected with the therapeutic polypeptide, which is expressed in cells into which it is introduced according to the invention methods. The polynucleotide may further encode a selectable marker polypeptide, such as is known in the art, useful in detecting transformation of cells with active agents according to the invention method.

In various embodiments of the invention method, the active agent can be a "proliferation-modulating agent," which alters the proliferative abilities of cells. Proliferation modulating agents include, but are not limited to, cytotoxic agents, agents toxic or becoming toxic in the presence of a protein, and chemotherapeutic agents. The term "cytotoxic agent" refers to a protein or other molecule having the ability to inhibit, kill, or lyse a particular cell. Cytotoxic agents include proteins such as ricin, abrin, diphtheria toxin, saporin, or the like. In one embodiment, the cytotoxic agent is only effective when it can gain access to the cell, such as by the introduction of the agent into the cell by needle-free injection in combination with electroporation. The introduction of such agents intracellularly, or the expression of nucleic acids encoding polypeptides intracellularly, results in inhibition of protein synthesis or death of the cell. Illustrative toxic subunits include the A chains of diphtheria toxin, enzymatically active proteolytic fragments from *Pseudomonas aeruginosa* exotoxin-A, ricin A-chain, abrin A-chain, modeccin A-chain, and proteins having similar activity found in various plants, such as the plants *Gelonium multiflorum, Phytolacca Americana, Croton, Tiglium, Jatropha, Curcas, Momordic, Charantia, Reachan*, the toxin saporin from *Saponaria officinalis* (Thorpe et al. *J. National Cancer Institute* (1985) 75:151), the Chinese cucumber toxin, trichosanthin (Yeung et al. Intl. *J. of Peptide Protein Res.* (1985) 27:325–333), and the like. Mutant species of the toxins also may be used, for example, CRM 45 (Boquet et al. *Proc. Natl. Acad. Sci. USA* (1976) 73:4449–4453).

In other embodiments, the active agent can be a "chemotherapeutic agent," having an antitumor or cytotoxic effect. Such agents can be "exogenous" agents, which are not normally found in the subject (e.g., chemical compounds and drugs). Chemotherapeutic agents can also be "endogenous" agents, which are native to the subject, including suitable naturally occurring agents, such as biological response modifiers (i.e., cytokines, hormones, and the like). Specific chemotherapeutic proliferation-modulating agents include, but are not limited to daunomycin, mitomycin C, daunorubicin, doxorubicin, 5-FU, cytosine arabinoside, colchicine, cytochalasin B, bleomycin, vincristine, vinblastine, methotrexate, and the like. Additional active agents that act as chemotherapeutic agents are cytotoxic agents, such as those derived from microorganism or plant sources.

Drugs contemplated for use in the invention method as the active agent include antibiotics such as are known in the art and chemotherapeutic agents having an antitumor or cytotoxic effect. Such drugs or agents include bleomycin, neocarcinostatin, suramin, doxorubicin, carboplatin, taxol, mitomycin C, cisplatin, and the like. Other chemotherapeutic agents will be known to those of skill in the art (see for example The Merck Index). In addition, agents that are "membrane-acting" agents can also be introduced into cells according to the invention method. Membrane acting agents are a subset of chemotherapeutic agents that act primarily by damaging the cell membrane, such as N-alkylmelamide, para-chloro mercury benzoate, and the like. Alternatively, the composition can include a deoxyribonucleotide analog, such as azidodeoxythymidine, dideoxyinosine, dideoxycytosine, gancyclovir, acyclovir, vidarabine, ribavirin, or any chemotherapeutic known to those of average skill in the art.

Vaccination is an effective form of preventative care against infectious diseases. Safe and effective vaccines are available to protect against a variety of bacterial and viral diseases. These vaccines may consist of inactivated pathogens, recombinant or natural subunits, and live attenuated or live recombinant microorganisms. Accordingly, in another aspect, an agent or composition introduced to the epidermis of a subject can be a vaccine, such as a vaccine that includes a polynucleotide or a protein component.

DNA immunization, a method to induce protective immune responses using "naked" DNA, complexed DNA or encapsulated DNA, is effective as shown in U.S. Pat. No. 5,589,466. DNA immunization entails the direct, in vivo administration of vector-based DNA or non-vector DNA that encodes the production of defined microbial or cellular antigens, for example, and cytokines (e.g., IL and IFN), for example. The de novo production of these antigens in the host's own cells results in the elicitation of antibody and cellular immune responses that provide protection against challenge and persist for extended periods in the absence of further immunizations. The unique advantage of this technology is its ability to mimic the effects of live attenuated vaccines without the safety and stability concerns associated with the parenteral administration of live infectious agents. Because of these advantages, considerable research efforts have focused on refining in vivo delivery systems for naked DNA that result in, for example, maximal antigen production and resultant immune responses. Such systems also include liposomes and other encapsulated means for delivery of DNA.

Accordingly, it is presently preferred that the DNA or RNA molecule introduced as a vaccine to induce a protective immune response encodes not only the gene product (i.e., active agent) to be expressed, but also initiation and termination signals operably linked to regulatory elements including a promoter and polyadenylation signal capable of directing expression in the cells of the vaccinated subject. The vaccine polynucleotide can optionally be included in a pharmaceutically acceptable carrier as described herein.

As used herein, the term "gene product" refers to a protein resulting from expression of a polynucleotide within the treated cell. The gene product can be, for example, an immunogenic protein that shares at least an epitope with a protein from the pathogen or undesirable cell-type, such as a cancer cell or cells involved in autoimmune disease against which immunization is required. Such proteins are antigens and share epitopes with either pathogen-associated proteins, proteins associated with hyperproliferating cells, or proteins associated with autoimmune disorders, depending upon the type of genetic vaccine employed. The immune response directed against the antigenic epitope will protect the subject against the specific infection or disease with which the antigenic epitope is associated. For example, a polynucleotide that encodes a pathogen-associated gene product can be used to elicit an immune response that will protect the subject from infection by the pathogen.

Likewise, a polynucleotide that encodes a gene product containing an antigenic epitope associated with a hyperproliferative disease such as, for example, a tumor-associated protein, can be used to elicit an immune response directed at hyperproliferating cells. A polynucleotide that encodes a gene product that is associated with T cell receptors or antibodies involved in autoimmune diseases can be used to elicit an immune response that will combat the autoimmune disease by eliminating cells in which the natural form of target protein is being produced. Antigenic gene products introduced into cells as active agents according to the present invention may be either pathogen-associated proteins, proteins associated with hyperproliferating cells, proteins associated with auto-immune disorders or any other protein known to those of average skill in the art.

In addition, it may be desirable to introduce into cells of a subject a polynucleotide that modulates the expression of a gene, such as an endogenous gene, in cells. The term "modulate" envisions the suppression of expression of a gene when it is over-expressed, as well as augmentation of expression when it is under-expressed. Where a cell proliferative disorder is associated with the expression of a gene, nucleic acid sequences that interfere with the gene's expression at the translational level can be used to modulate gene expression. This approach introduces into the cells of a subject such active agents as antisense nucleic acid sequences, ribozymes, or triplex agents to block transcription or translation of a specific mRNA, either by masking that mRNA with an antisense nucleic acid or triplex agent, or by cleaving it with a ribozyme.

Antisense nucleic acid sequences are DNA or RNA molecules that are complementary to at least a portion of a specific mRNA molecule (Weintraub, *Scientific American,* 262:40, 1990). In the cell, the antisense nucleic acid hybridizes to the corresponding mRNA, forming a double-stranded molecule. The antisense nucleic acid interferes with the translation of the mRNA, since the cell will not translate a mRNA that is double-stranded. Antisense oligomers of about 15 nucleotides are preferred, since they are easily synthesized and are less likely than larger molecules to cause problems when introduced into the target cell. The use of antisense methods to inhibit the in vitro translation of genes is well known in the art (Marcus-Sakura, *Anal. Biochem.,* 172:289, 1988).

Use of a short oligonucleotide sequence (i.e., "triplex agent") to stall transcription is known as the triplex strategy, since the oligomer winds around double-helical DNA, forming a three-strand helix. Therefore, such triplex agents can be designed to recognize a unique site on a chosen gene (Maher, et al., *Antisense Res. and Dev.,* 1(3):227, 1991; Helene, C., *Anticancer Drug Design,* 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences that are four bases in length, while "hammerhead"-type ribozymes recognize base sequences that are 11–18 bases in length. The longer the recognition sequence, the greater the likelihood that the sequence will occur exclusively in the target mRNA species. Consequently, it is preferred to employ hammerhead-type ribozymes over tetrahymena-type ribozymes for inactivating a specific mRNA species, and 18-based recognition sequences are preferable to shorter recognition sequences as active agents in practice of the invention methods.

The active agent introduced according to the invention methods can also be a therapeutic peptide or polypeptide. For example, immunomodulatory agents and other biological response modifiers can be administered for incorporation by cells. The term "biological response modifiers" is meant to encompass substances which are involved in modifying the immune response. Examples of immune response modifiers include such compounds as lymphokines. Lymphokines include tumor necrosis factor, interleukins 1, 2, and 3, lymphotoxin, macrophage activating factor, migration inhibition factor, colony stimulating factor, and alpha-interferon, beta-interferon, and gamma-interferon, their subtypes and the like.

Also included are polynucleotides which encode metabolic enzymes and proteins, including anti-angiogenesis compounds, e.g., Factor VIII or Factor IX. The active agent introduced according to the invention methods can also be an antibody. The term "antibody" as used herein is meant to include intact molecules as well as fragments thereof, such as Fab and F(ab')$_2$, and the like, as are known in the art.

In addition, the composition can include a detectable marker, such as a radioactive label. Alternatively, the composition can include a photoactive modification, such as Psoralin C2. Further, the composition can include a phosphoramidate linkage, such as butylamidate, piperazidate, and morpholidate. Alternatively, the composition can include a phosphothiolate linkage or ribonucleic acid. These linkages decrease the susceptibility of oligonucleotides and polynucleotides to degradation in vivo.

The term "pharmaceutical agent" or "pharmaceutically active agent" as used herein encompasses any substance that will produce a therapeutically beneficial pharmacological response when administered to a subject, including both humans and animals. More than one pharmaceutically active substance may be included, if desired, in a pharmaceutical composition used in the method of the present invention.

The pharmaceutically active agent can be employed in the present invention in various forms, such as molecular complexes or pharmaceutically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium) and the like. Furthermore, derivatives of the active substances such as esters, amides, and ethers which have desirable retention and release characteristics but which are readily hydrolyzed in vivo by physiological pH or enzymes can also be employed.

As used herein, the term "therapeutically effective amount" or "effective amount" means that the amount of the biologically active or pharmaceutically active substance is of sufficient quantity and activity to induce a desired pharmacological effect. The amount of substance can vary greatly according to the effectiveness of a particular active substance, the age, weight, and response of the individual subject as well as the nature and severity of the subject's condition or symptoms. Accordingly, there is no upper or lower critical limitation upon the amount of the active agent introduced into the cells of the subject although it is generally a greater amount than would be delivered by passive absorption or diffusion, but should not be so large as to cause excessive adverse side effects to the cell or tissue containing such cell, such as cytotoxicity, or tissue damage. The amount required for transformation of cells will vary from cell type to cell type and from tissue to tissue and can readily be determined by those of ordinary skill in the art using the teachings herein. The required quantity to be employed in practice of invention methods can readily be determined by those skilled in the art.

In one embodiment of the invention method, the amount of active agent such as a nucleic acid sequence encoding a gene product introduced into the cells is a "transforming amount." A transforming amount is an amount of the active agent effective to modify a cell function, such as mitosis or gene expression, or to cause at least some expression of a gene product encoded by the nucleic acid sequence.

Introduction of active agents across the natural barrier layer of skin or mucous membrane can be enhanced by encapsulating the active agent in a controlled release vehicle or mixed with a lipid. As used herein with respect to preparations or formulations of active agents, the term "controlled release" means that the preparation or formulation requires at least an hour to release a major portion of the active substance into the surrounding medium, for example, about 1–24 hours, or even longer.

Preferred controlled release vehicles that are suitable for electrotransport are colloidal dispersion systems, which include macromolecular complexes, nanocapsules, microcapsules, microspheres, beads, and lipid-based systems, including oil-in-water emulsions, micelles, mixed micelles, liposomes, and the like. For example, in one embodiment, the controlled release vehicle used to contain the active agent for injection is a biodegradable microsphere. Microspheres wherein a pharmaceutically active agent is encapsulated by a coating of coacervates is called a "microcapsule."

Liposomes, which may typically bear a cationic charge, are artificial membrane vesicles useful as delivery vehicles in vitro and in vivo. It has been shown that large unilamellar vesicles (LUV), which range in size from about 0.2 to 4.0 μm, can encapsulate a substantial percentage of an aqueous buffer containing large macromolecules, such as DNA.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations, making them suitable vehicles for encapsulating an active agent intended to undergo electrotransport according to the invention methods.

Examples of lipids useful in liposome production include phosphatidyl compounds, such as phosphatidylglycerol, phosphatidylcholine, phosphatidylserine, phosphatidylethanolamine, sphingolipids, cerebrosides, gangliosides, and the like. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoyl-phos-phatidylcholine.

Preparations suitable for electrotransport may also include a "pharmaceutically acceptable carrier." Such carriers include sterile aqueous or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, fixed oils, and the like. Vehicles suitable for intercellular or intracellular injection may also include fluid and nutrient replenishers, electrolyte replenishers, such as those based on Ringer's dextrose, and the like. Preservatives and other additives may also be present such as, for example, antimicrobials, anti-oxidants, chelating agents, and inert gases, and the like.

The invention method may optionally further comprise pretreatment of the tissue surface with compounds or compositions that facilitate injection of the active agent into cells underlying the tissue surface. Examples of components of a composition suitable for pretreatment of the epidermis of the subject include, for example, a reducing agent, such as a charged reducing agent (e.g., DMSO) that disrupts cross linked keratin within keratinocytes of the epidermis. Alternatively, the epidermis can be pretreated by application of a proteinase, such as keratinase, papain, or reducing agents or compounds, to overcome possible hindrance of DNA transport during injection and electroporation that might be caused by the dense keratin matrix of the epidermis.

As used herein, the term "subject" refers to any animal. It is envisioned that the methods for delivering an agent into cells of a subject can be performed on any animal, including domesticated animals kept as pets, as well as animals raised as workers or as a providers or sources of food. Preferably, the subject is a human.

As used herein, the term "local," when used in reference to an active agent introduced by a needle-free injector according to the invention method, refers to activity within the region of tissue treated (e.g., the region electroporated). Thus, an agent injected into skin or mucosal tissue is believed to be taken up by cells underlying or contiguous with the skin or mucosal tissue and to exert its biological or pharmaceutical activity within the cells of the tissue or muscle directly underlying the skin. Nevertheless, the skilled artisan will recognize that some biologically active agents introduced according to the invention method may have a systemic effect or activity, such that, after being injected into a particular region of tissue according to the invention method, the agent may be distributed at least in part to other areas of the subject, thereby producing or contributing to a systemic effect.

The invention methods for introducing an agent into cells are useful in treatment of a variety of conditions and diseases ranging from diabetes to psoriasis and baldness. Like other types of transdermal drug delivery, the invention methods have application in treatment of conditions that have a large potential market, such as pain management (acute and chronic), treatment of erectile dysfunction, skin aging, and the like. For example, in one aspect, the invention method is useful in treating undesired cells. An "undesired cell" is any cell targeted for removal due to its location, genotypic and/or phenotypic properties, and the like. Examples of conditions exhibiting undesired cells that can be treated using the invention methods include, but are not limited to, the presence of excess fat cells, endometrial tissue in endometriosis, excess tissue caused by psoriasis, birth marks such as port wine stains, adhesions or scar tissue from injury or surgery, moles, and the like.

The methods of the invention are useful in treating cell proliferative disorders or other disorders of the various organ systems, particularly, for example, cells in the skin, mucosal tissue uterus, prostate and lung, and also including cells of heart, kidney, muscle, breast, colon, prostate, thymus, testis, ovary, blood vessel and the like. The term "cell proliferative disorder" refers to a disease or condition characterized by inappropriate cell proliferation, and includes neoplasia. Concepts describing normal tissue growth are applicable to malignant tissue since normal and malignant tissues can share similar growth characteristics, both at the level of the single cell and at the level of the tissue. In tumors, production of new cells exceeds cell death. For instance, a neoplastic event tends to produce an increase in the proportion of stem cells undergoing self-renewal and a corresponding decrease in the proportion progressing to maturation (McCulloch, E. A., et al., *Blood* 59:601–608, 1982). Thus, the term "cell proliferative disorder" denotes malignant as well as non-malignant cell populations, which often appear to differ from the surrounding tissue both morphologically and genotypically. Specific non-limiting examples of non-malignant cell proliferative disorders include warts, benign prostatic hyperplasia, skin tags, and non-malignant tumors. For example, the invention can be used to treat such cell proliferative disorders as benign prostatic hyperplasia or unwanted genital warts by targeting the undesirable cells that characterize such conditions for removal.

The methods of the invention are advantageous in several respects. First, the invention methods allow, for example, topical treatment of skin or mucosal lesions, such as melanoma. Such treatment is not invasive and delivery of pharmaceutical compounds, polynucleotides or other agents can be localized to the site of the lesion. Further, the amount of agent necessary to treat a particular lesion is significantly reduced by localized application of the agent, thereby substantially diminishing the cost of treatment and side effects. In addition, risk of infection and mechanical trauma, such as that caused by subcutaneous injections, is avoided by using electroporation in combination with needle-free injection. Further, risk associated with disrupting cancer cells, such that they are dislodged from a primary location, thereby spreading the cancer, is lessened. In addition, systemic illnesses can be treated by delivery of pharmaceuticals, polynucleotides, such as antisense oligonucleotides, or other agents, to control expression of a targeted gene associated with the illness over an extended period of time.

One therapeutic application of electroporation includes needle-free introduction of a cytotoxic agent into tissue and electroporation of the agent into cells by applying voltage pulses between electrodes or electrically conductive needle-free injectors disposed on opposite sides of or within the tissue. Another therapeutic application of the invention methods includes needle-free injection of a nucleic acid encoding a cytotoxic agent into tissue having undesirable cell types (i.e. cells proliferating in an unnatural manner) and electroporation of the nucleic acid into the cells of the tissue by applying voltage pulses between electrodes strategically located on opposite sides or within the tissue containing undesirable cells. As disclosed herein, it is preferred that the needle-free jet injection device itself serves as an electrode. (See FIGS. 1A and B). However, when the injector is not used as an electrode, caliper or surface electrodes are utilized.

The invention methods can also be used in practice of gene therapy for the treatment of cell proliferative or immunologic disorders mediated by a particular gene or absence thereof. Such therapy would achieve its therapeutic effect by introduction of a specific sense or antisense polynucleotide into cells having the disorder. Polynucleotides intended for introduction into cells of a subject for the purpose of gene therapy can be contained in a recombinant expression vector such as a chimeric virus, or the polynucleotide can be delivered as "naked" DNA as described herein.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (-MoMuLV), Harvey murine sarcoma virus (HaMuS-V), murine mammary tumor virus (-MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated.

The invention will now be described in greater detail by reference to the following, non-limiting examples.

EXAMPLE 1

The following study was conducted to compare quantatively the level of gene expression when a DNA-containing plasmid is administered by intradermal injection and by needle-free injector. Electroporation of the injection site at various voltage levels was used to determine and compare electroporation enhancement of gene expression when DNA is injected by the two methods tested.

I. Luciferase reporter gene. To quantify the level of gene expression, the luciferase reporter gene was used in the first study.

Animals. Four to six week old male and female outbred pigs weighing 20 to 40 pounds were purchased from the Prairie Swine Center (University of Saskatchewan, Saskatoon, Saskatchewan). The animals were housed and treated in compliance with the Canadian Council for Animal Care. Animals were randomly assigned to six groups of five animals each.

Electroporation. To determine the effect of electroporation on expression of plasmid DNA, electroporation was performed using the BTX ECM 830 Pulse Generator with the needle-free micropatch round electrode mounted on a handle (model MP 35) (Genetronics, San Diego, Calif.). Six square-wave pulses were applied at 60, 70, or 80 V, with pulse duration of 60 msec, pulse interval of 200 msec, and reversal of polarity after three pulses.

Luciferase expression and assay. A luciferase encoding plasmid (Pmas-luc) under the control of the CMV promoter in the pMAS backbone (Krieg, A. M., et al., Proc. Natl. Acad. Sci. USA. 95:12631–6.) was a gift from Dr. Heather Davis (University of Ottawa, Ontario, Canada) (Weeratna, R., et al., Antisense Nucleic Acid Drug Dev. 8:351–356). Plasmid DNA encoding luciferase was injected intradermally using a 26-gauge needle or a DERMAL BIOJECT™ needle-free injection system (BioJect, Inc., Portland, Oreg.), followed by electroporation with various voltages. Intradermal needle injection was tested with no electroporation and with electroporation at voltages of 60V and 80V. Needle-free using the Bioject device was tested with no electroporation and with electroporation at voltages of 60 V, 70 V, and 80 V.

For each injection, a dose of 100 µg of pMAS-luc (Weeratna et al., supra) in 100 µl phosphate buffered saline (PBS) was administered into the skin of the shaved abdomens (eight sites per pig), with each treatment group having four sites from the same pig. The luciferase-encoding plasmid was injected at eight distinct sites, and electroporation was applied to four of those sites. Forty-eight hours after the administration of the plasmid, the area surrounding each injection site was biopsied with an 8-mm diameter puncher at a depth of approximately 8-mm. Skin was homogenized in 500 µl lysis buffer (Promega, Madison, Wis.) with a POLYTRON® homogenizer (Brinkmann Instruments, Rexdale, Ontario) to produce protein extracts. Luciferase activity in the protein extracts was determined using Promega's luciferase assay system. On a Packard PICOLITE® luminometer (Packard Instruments Canada LTD, Mississauga, Ontario), the bioluminescence of each 500-µl sample was counted for 30 seconds and recorded as relative light units (RLUs). Untreated or PBS-injected tissues were used to determine the background luminescence levels.

Histological examination of skin. Forty-eight hours after intradermal injection of 100 µl PBS alone or PBS containing 100 µg of DNA using the needle-free injection system and electroporation with 60 V, 70 V, or 80 V, skin biopsies were fixed in 10% formalin. Tissues were embedded in paraffin and 2-µm sections were stained with hematoxylin/eosin (H&E).

Histological examination of tissue sections was used to determine how voltage could influence gene expression. The results of histological examination showed that increasing the voltage increases the amount of tissue damage and cellular infiltration of the skin. The optimal voltages determined were 60V for intradermal needle injection and 70V for the needle-free deliveries. Thus, proper voltage selection for the DNA immunizations enhanced cellular uptake of plasmid and minimized tissue damage.

Figure 3:
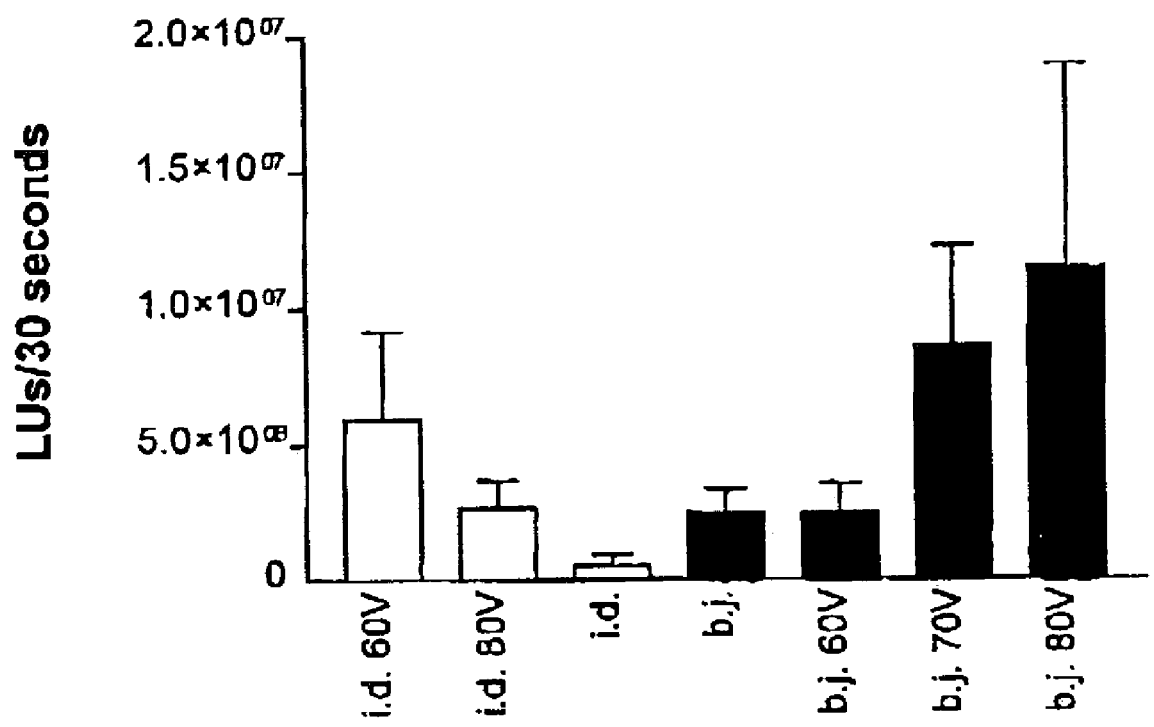
FIG. 3 is a graph showing electroporation used in conjunction with intradermal injection of DNA vaccine improves gene expression levels. Intradermal expression levels are shown for DNA vaccine injected using needle-free BioJect (b.j.) and needle (i.d.n.) injections, without or with electroporation, at the voltages indicated. Error bars represent standard error of the mean (SEM).

The luciferase assay results indicated that delivery by needle-free injector consistently outperformed needle injections, with or without electroporation. However, electroporation significantly enhanced the level of expression with both types of injection (FIG. 3). From the results of these studies, it can be concluded that the optimal voltage to accompany needle injection is lower than the optimal voltage to accompany injection with a needle-free injector.

II. GFP gene expression. To analyze localization of gene expression a plasmid encoding green fluorescent protein (GFP) was used. A plasmid encoding GFP under the control of the CMV promoter was obtained through Quantum Biotechnologies, (Montreal, Que.). 100 µg of the plasmid in 100 µl PBS was administered intradermally at the sites on the shaved abdomens of the pigs using a syringe or needle-free injector in combination with electroporation (60 V for syringe injection and 70 V for needle-free administration). Twenty-four hours after administration the injection site was biopsied using an 8-mm punch. Skin samples were frozen in liquid nitrogen and stored at −70° C. until they were sectioned. Skin samples were cut transversally with an IEC MINITOME® microtome cryostat (Damon, Needham, Miss.) into 7-µm sections. Sections containing GFP expressing cells were photographed with an Olympus AH2-RFL microscope using standard light together with blue fluorescent light. The results were based on four skin punch biopsies per treatment.

The results of histological examination of tissue samples showed that delivery of plasmid by either intradermal injection or needle-free injector resulted in GFP expression surrounding the injection site in the epidermis. However, delivery with the needle-free injector resulted in consistent GFP expression in skin biopsies with GFP expression in all four biopsies; whereas the results of intradermal needle injection was not consistent, since GFP was only detected in one out of four biopsies. In addition, administration by needle-free injector resulted in GFP expression in cells surrounding the hair follicles, where dendritic cells are known to be numerous. Since dendritic cells are active sites of immunological activity, it can be expected that needle free injection will be a good route of administration DNA vaccines.

Electroporation influenced the localization of GFP with a much greater dispersion of GFP in the dermis away from the injection site following both intradermal needle administration and needle-free injector administration. Delivery by needle-free injector in combination with electroporation (70 volts) resulted in GFP expression only in the deeper layers of the skin and was not detected under the damaged stratum corneum. In a single isolated biopsy, GFP expression following intradermal needle injection looked more robust and wide spread compared to needle-free administration. All other biopsies showed that needle-free injection administration resulted in gene expression and, and more importantly, the gene expression was distributed in a much wider area than resulted from intradermal needle injection.

EXAMPLE 2

To study the effects of electroporation in the context of a DNA vaccine, a DNA-prime/DNA-boost/protein-boost strategy was evaluated for enhancement of immune responses in large animals, and compared the responses achieved following standard protein vaccination. The strategy used resembled DNA-prime/protein-boost strategies previously used in non-human primates, which yielded outstanding results for both malaria (12) and HIV vaccinations (1).

Immunization protocols. For immunization studies, animals were selected and care for as above. Pigs were randomly assigned to six groups of five animals each. The pigs were anesthetized with halothane prior to DNA injection and electroporation and treated as follows: The animals in Group 1 each received 250 µg pHBsAg in 100 µl 0.1 M phosphate buffered saline (PBS) by a dermal BIOJECT B 2000° needle-free injection device (Bioject, Inc. Portland, Oreg.) at each of two abdominal sites for a total of 500 µg pHBsAg. The animals in Group 2 were treated identically to those in Group 1, except that the injection sites were also treated with 70 V electroporation, immediately following plasmid injection. The animals in Group 3 each received 250 µg pHBsAg in 100 µl PBS by an intradermal injection at each of two abdominal sites for a total of 500 µg pHBsAg. The animals in Group 4 were treated identically to those in Group 3 except that injection sites were treated with a 60 V electroporation, immediately following plasmid administration. Animals in Group 5 received 500 µl of the commercial hepatitis B vaccine (Engerix-B, SmithKline Beecham Pharma, Oakville, Ont.) injected intradermally with the Bioject device in two 250 µl doses on the abdomen and Group 6 was immunized with Engerix-B by an intramucular injection. All animals were boosted with the same injection conditions after four weeks. All treatment groups were boosted at week eight with Engerix B vaccine by intramuscular injection for all groups except group 5, which was injected with Engerix using the Bioject device as previously described (Table 1).

TABLE 1

EXPERIMENTAL DESIGN

| Group[1] | Vaccine | 1st and 2nd immunizations[2] Route/Method | Voltage (V) | 3rd immunization[3] (Engerix-B) Route/Method |
|---|---|---|---|---|
| 1 | pHBsAg | i.d./BioJect | — | i.m./needle |
| 2 | pHBsAg | i.d./BioJect | 70 V | i.m./needle |
| 3 | pHBsAg | i.d./needle | — | i.m./needle |
| 4 | pHBsAg | i.d./needle | 60 V | i.m./needle |
| 5 | Engerix-B | i.d./BioJect | — | i.d./BioJect |
| 6 | Engerix-B | i.m./needle | — | i.m./needle |

[1] Each group consisted of five animals.
[2] First and second immunizations were administered on day zero and four weeks later.
[3] The third immunization was given eight weeks after the first immunization i.d., intradermal; i.m., intramuscular.

To assess efficacy of DNA vaccination in priming the immune system, animals in all experimental groups were boosted with a protein vaccine at week 8 post initial injection.

Measurement of humoral responses. At four, eight, and ten weeks after the first immunization serum was collected from anesthetized animals and centrifuged for analysis. Anti-HBsAg antibodies were quantitatively measured using the AUSAB EIA Diagnostic Kit, and quantification in milli-International Units/ml was performed in parallel with the AUSAB Quantification Panel, according to the manufacturer's instructions (Abbott Laboratories, North Chicago, Ill.).

Anti-hepatitis B $IgG_1$ and IgG2 isotypes were identified by ELISA as follows. IMMUNLON 2® ELISA plates (Dynex, Chantilly, Va.) were coated with HBsAg (BioDesign International, Saco, Me.) (1 µg/ml in 20 mM $Na_2CO_3$) and stored overnight at 4° C. Then, the plates were washed with phosphate-buffered saline-Tween (PBST) (PBS, 0.05% TWEEN 20®; Sigma Chemical Co., St. Louis, Mo.). Serum was diluted in diluent (PBST, 0.5% gelatin) (Sigma) 20-fold, followed by serial 4-fold dilutions, and incubated overnight at 4° C. Plates were washed six times in PBST. Porcine $IgG_1$ and $IgG_2$ isotypes were detected using mouse anti-porcine antibodies specific against $IgG_1$ and IgG2 isotypes (Serotec, Hornby, Ontario). Following incubating at room temperature for one hour, plates were washed six times in PBST. Anti-mouse $IgG_1$ biotinylated antibodies (Caltag, Toronto, Ontario), diluted in diluent, were added and incubated for one hour. Plates were washed six times in PB ST, and streptavidin-alkaline phosphatase (Jackson Immuno-Research Labs, West Grove, Pa.) was added to the plates and incubated for one hour. The alkaline phosphatase activity was measured by the conversion of p-nitrophenol phosphate (PNPP) (Sigma). The absorbance was read after 15 to 20 minutes at 405-nm wavelength (Bio-Rad, Hercules, Calif.).

Figure 4:
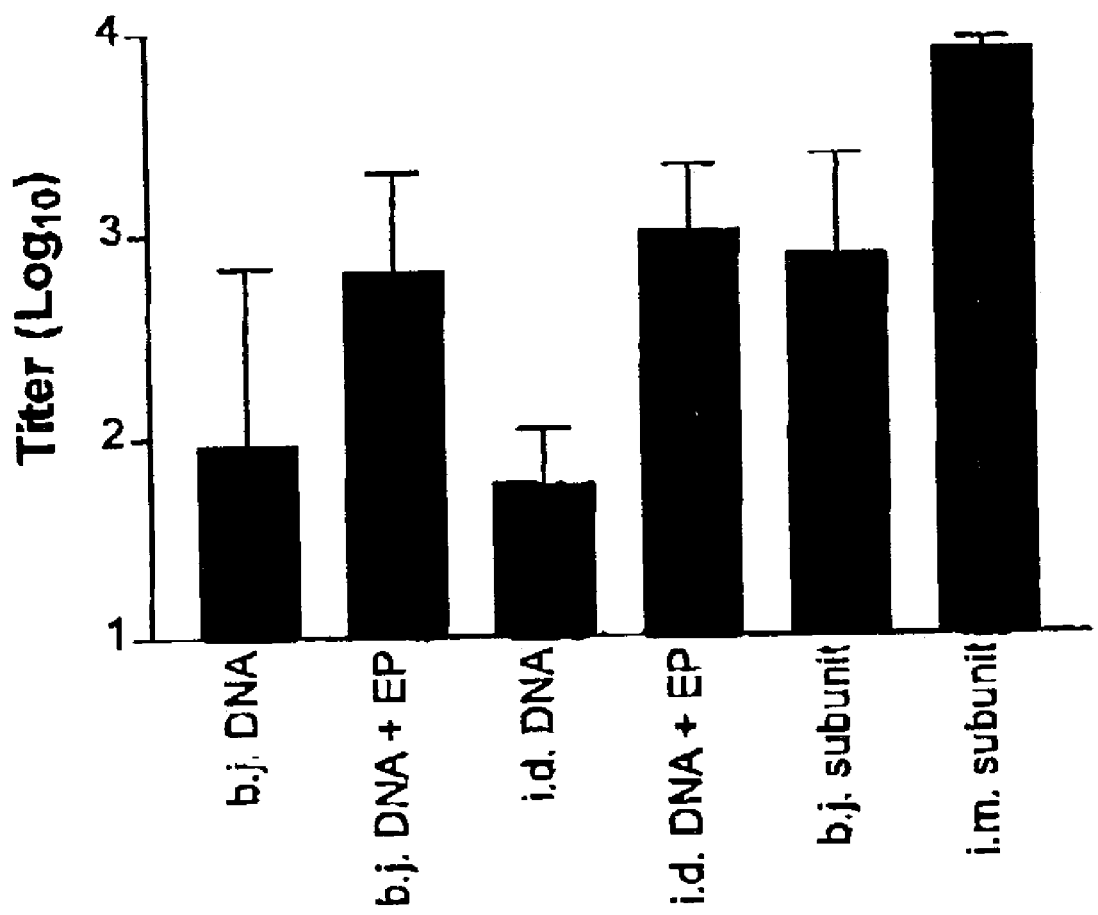
FIG. 4 is a graph showing immune responses to Hepatitis B after various combinations of DNA vaccine followed by protein booster immunizations. HBsAg antibody titers at 10 weeks were determined using the AUSAB EIA and titers shown are the geometric mean of 5 animals for all the groups except for the i.m. subunit group, which had 4 animals. Error bars are SEM.
Figure 5A:
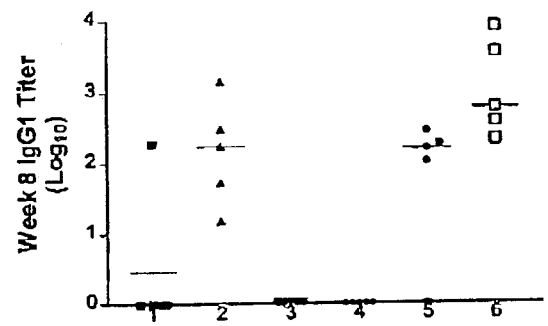
FIGS. 5A–5D are graphs showing antibody isotype responses elicited by Hepatitis B immunizations according to the invention methods. Data represent Hepatitis B specific IgG1 and IgG2 titers at 8 and 10 weeks for individual animals. The bar represents the geometric mean. Group 1=needle-free injection of DNA, Group 2=needle-free injection of DNA+electroporation (EP), Group 3=intradermal injection of DNA, Group 4=intradermal injection of DNA+EP, Group 5=needle-free administration of the subunit vaccine control, and Group 6=intramuscular injection of the subunit vaccine control.
Figure 5B:
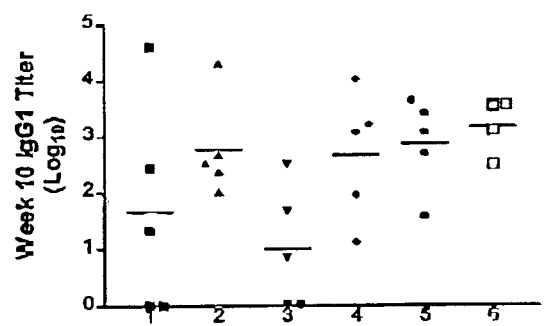
Figure 5C:
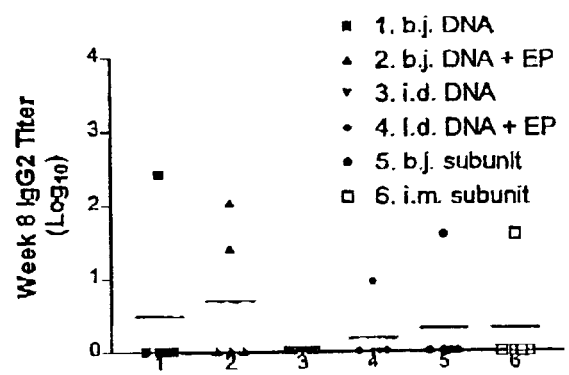
Figure 5D:
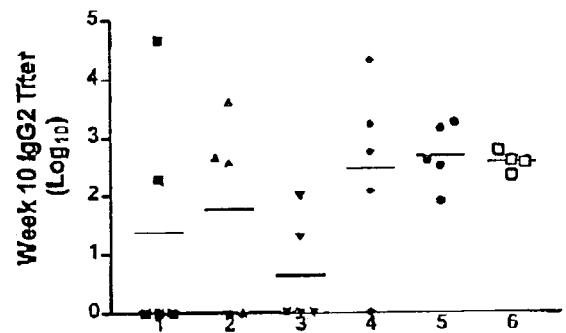

Immune Responses in Immunized Pigs. Although there was variability in the immune response among the animals in each group described above, the animals treated with electroporation showed better immune responses than the non-electroporated animals, based on both the number of animals responding and the level of response recorded by AUSAB (Table 2 below and FIG. 4).

TABLE 2

Responses in Pigs to Various Hepatitis B Vaccinations[1]

| | Number of Animals Responding | | | | | |
|---|---|---|---|---|---|---|
| | Week 4 | | Week 8 | | Week 10 | |
| Vaccine Group | AUSAB | ELISA | AUSAB | ELISA | AUSAB | ELISA |
| (1) DNA, b.j. | 0/5 | 0/5 | 1/5 | 1/5 | 4/5 | 3/5 |
| (2) DNA, b.j. + EP | 0/5 | 0/5 | 2/5 | 5/5 | 5/5 | 5/5 |
| (3) DNA, i.d.n. | 0/5 | 0/5 | 0/5 | 0/5 | 5/5 | 3/5 |
| (4) DNA, i.d.n. + EP | 0/5 | 0/5 | 0/5 | 1/5 | 5/5 | 5/5 |
| (5) Engerix B, b.j. | 0/5 | 0/5 | 4/5 | 4/5 | 5/5 | 5/5 |
| (6) Engerix B, i.m.n. | 0/5 | 0/5 | 5/5 | 5/5 | 4/4 | 4/4 |

[1] The number of animals that showed an immune response out of the total number of animals in a group is indicated.
b.j. = Bioject needle-free injection; EP = electroporation; i.d.n. = intradermal needle; i.m.n. = intramuscular needle.

The results summarized in Table 2 are consistent with the results of the luciferase experiments of Example 1 herein, which indicated that electroporation enhances gene expression, and that needle-free delivery is more effective than needle delivery. These results also demonstrate the superiority of immune responses elicited with the combination of needle-free delivery and electroporation over responses achieved by intradermal needle injections, both with respect to the number of animals responding and the magnitude of the response.

As a positive control for these studies, two groups of animals were immunized with a subunit vaccine injected either intramuscularly with needle and syringe (the prior art route) or intradermally with the needle-free injector. Results of the control studies indicate that the intramuscular needle injection resulted in more robust immune responses than injection with the needle-free injector.

Results in Table 2 also demonstrate that even though immune responses were undetectable in most of the animals after two rounds of DNA immunization, the majority responded rapidly to a protein boost. The fact that nearly all DNA immunized animals responded within two weeks of the protein boost demonstrates an anamnestic response, since the protein vaccine alone did not induce immune responses 4 weeks post immunization (Table 2).

To determine whether the experimental manipulations had an impact on the antibody isotypes generated, the sera were analyzed for the presence of anti-HBsAg $IgG_1$ and $IgG_2$ using an ELISA. As shown in FIGS. 5A–5D, in those animals mounting an early response, most produced primarily $IgG_1$ at 8 weeks. However, after boosting with protein, a much more balanced response with approximately equivalent levels of $IgG_1$ and $IgG_2$ were evident. Additionally, the groups injected with DNA and treated with electroporation (Groups 2 and 4) produced antibodies similar in titer to those in the cohorts receiving multiple protein injections (Groups 5 and 6). In contrast, those groups that received DNA without electroporation (Groups 1 and 3) produced antibodies of lower titer, even after the protein boost.

It will be apparent to those skilled in the art that various modifications and variations can be made to the compounds and processes of this invention. Thus, it is intended that the present invention cover such modifications and variations, provided they come within the scope of the appended claims. Accordingly, the invention is limited only by the following claims.

What is claimed is:

1. A method for introducing a biologically active agent into cells in a region of tissue of a subject, said method comprising:
  a) using one or more needle-free injectors of an electroporation device to inject said agent into said region in a form suitable for electrotransport, wherein said electroporation device comprises:
    i. a needle-free injector configured to serve as a first electroporation electrode when positioned in contact with tissue of the subject:
    ii. a second electroporation electrode disposed in spaced relation to said first electroporation electrode:
    iii. an energy source in electrical communication with said first and second electroporation electrodes to energize said first and second electroporation electrodes to effect electroporation; and
  b) using said electroporation device to generate an electric field sufficient to electroporate cells of said region, wherein said electroporating is conducted prior to, simultaneously with, and/or subsequently to injecting said agent into said region using at least one of said needle-free injectors to introduce the biologically active agent into said subject,
  whereby the combination of needle-free injection and electroporation is sufficient to introduce the agent into the cells.

2. The method of claim 1, wherein the electric field is generated by a square, rectangular, triangular, or exponential decay wave pulse.

3. The method of claim 2, wherein the pulse is of at least 50 about V.

4. The method of claim 2, wherein the pulse is from about 100 μsec to about 100 msec.

5. The method of claim 2, wherein the pulse is monopolar or bipolar.

6. The method of claim 1, wherein the injection of the agent is simultaneous with application of the electric field wherein the needle-free injector acts as an electrode.

7. The method of claim 1, wherein the electroporation device comprises at least two needle-free injectors and the electric field is applied by contacting said region with at least two of the needle-free injectors in spaced apart relation, with one of the needle-free injectors serving as a donor electrode and the other serving as a receptor electrode.

8. The method of claim 1, wherein application of the electric field and injection of the agent is substantially simultaneous.

9. The method of claim 1, wherein the agent is in the form of a conductive liquid.

10. The method of claim 9, wherein the conductive liquid is contained in a partially ionized solvent.

11. The method of claim 1, wherein the agent is contained within a controlled release vehicle.

12. The method of claim 1, wherein the method is performed in vivo.

13. The method of claim 1, wherein the subject is a mammal.

14. The method of claim 1, wherein the subject is a human.

15. The method of claim 1, wherein the agent is a therapeutic agent.

16. The method of claim 15, wherein the therapeutic agent is selected from the group consisting of a chemotherapeutic agent, a polynucleotide, a polypeptide, and a peptide.

17. The method of claim 15, wherein the therapeutic agent is a chemotherapeutic agent is selected from the group consisting of bleomycin, neocarcinostatin, carboplatin, cisplatin, suramin, doxorubicin, mitomycin C, cisplatin, and a combination of any two or more of the foregoing compounds.

18. The method of claim 15, wherein the therapeutic agent is a nucleic acid construct encoding a homologous or heterologous gene product.

19. The method of claim 18, wherein the cells are transfected with the nucleic acid construct so that the gene product is expressed in the cells.

20. The method of claim 18, wherein the nucleic acid construct is an expression vector.

21. The method of claim 20, wherein the homologous or heterologous nucleic acid of the expression vector encodes a gene product and is operably linked to a suitable promoter sequence.

22. The method of claim 18, wherein the gene product is expressed in the cells.

23. The method of claim 15, wherein the therapeutic agent is an antibody.

24. The method of claim 15, wherein the therapeutic agent is an antibiotic.

25. The method of claim 1, wherein the agent is selected from the group consisting of a hormone, a cytokine, a lymphokine, a growth factor, and a combination of any two or more of the foregoing compounds.

26. The method of claim 1, wherein the agent is injected through a layer of skin into tissue underlying the skin and wherein the cells are muscle cells.

27. The method of claim 1, wherein the agent is mixed with a lipid.

28. The method of claim 1, wherein the tissue is skin.

29. The method of claim 1, wherein the agent is introduced encapsulated in a liposome or mixed with a charged lipid.

30. The method of claim 1, wherein the agent is in a liquid and the injector forces the liquid into the tissue as a conductive or essentially non-conductive liquid jet.

31. The method of claim 30, wherein the liquid jet acts as an electrode.

32. The method of claim 1, wherein the method further comprises applying iontophoresis to the tissue.

33. The method according to claim 1, wherein the agent is a proliferation-modulating agent.

34. The method according to claim 33, wherein the proliferation-modulating agent is selected from the group consisting of an antisense nucleic acid sequence, a ribozyme, a nucleic acid sequence, a triplex agent, and a combination of any two or more of the foregoing compounds.

35. The method according to claim 33, wherein the method is intended to treat or prevent a cell-proliferative disorder or condition in the subject.

36. The method according to claim 1, wherein the active agent comprises at least one antigenic epitope.

37. The method according to claim 36, wherein introduction of the agent is used to generates a protective immune response in the subject.

38. A method for intramuscular administration of a biologically active agent into cells in a region of muscle tissue of a subject, said method comprising:
   a) using one or more needle-free injectors of an electroporation device to introduce said agent into said region in a form suitable for electrotransport, wherein said electroporation device comprises:
      i. at least one needle-free injector, wherein at one of said needle-free injectors is configured to serve as a first electroporation electrode when positioned in contact with tissue of said subject:
      ii. a second electroporation electrode disposed in spaced relation to said first electroporation electrode; and
      iii. an energy source in electrical communication with said first and second electroporation electrodes to energize said first and second electroporation electrodes to effect electroporation; and
   b) using said electroporation device to generate an electric field sufficient to electroporate cells of said region, wherein said electroporating is conducted prior to, simultaneously with, and/or subsequently to introducing said agent into said region using at least one of said needle-free injectors to introduce the biologically active agent into said-subject,
   whereby the combination of needle-free injection and electroporation is sufficient to introduce the agent into the cells.

39. The method of claim 38, wherein the electric field is generated by a square, rectangular, triangular, or exponential decay wave pulse.

40. The method of claim 39, wherein the pulse is of at least about 50 V.

41. The method of claim 39, wherein the pulse is from about 100 µsec to about 100 msec.

42. The method of claim 39, wherein the pulse is monopolar or bipolar.

43. The method of claim 38, wherein introduction of the agent is simultaneous with application of the electric field, and wherein a needle-free injector acts as an electrode.

44. The method of claim 38, wherein the electric field is applied by contacting said region with an electroporation device that comprises at least two needle-free injectors in spaced apart relation, with one of the injectors serving as a donor electrode and the other serving as a receptor electrode.

45. The method of claim 38, wherein application of the electric field and injection of the agent is substantially simultaneous.

46. The method of claim 38, wherein the agent is in the form of a conductive liquid.

47. The method of claim 46, wherein the agent is contained in a partially ionized solvent.

48. The method of claim 38, wherein the agent is contained within a controlled release vehicle.

49. The method of claim 38, wherein the method is performed in vivo.

50. The method of claim 38, wherein the subject is a mammal.

51. The method of claim 38, wherein the subject is a human.

52. The method of claim 38, wherein the agent is a therapeutic agent.

53. The method of claim 52, wherein the therapeutic agent is selected from the group consisting of a chemotherapeutic agent, a polynucleotide, a polypeptide and a peptide.

54. The method of claim 52, wherein the therapeutic agent is a chemotherapeutic agent selected from the group consisting of bleomycin, neocarcinostatin, carboplatin, cisplatin, suramin, doxorubicin, mitomycin C, cisplatin, and a combination of any two or more of the foregoing compounds.

55. The method of claim 52, wherein the therapeutic agent is a nucleic acid construct encoding a homologous or heterologous gene product.

56. The method of claim 55, wherein the cells are transfected with the nucleic acid construct so that the gene product is expressed in the cells.

57. The method of claim 55, wherein the nucleic acid construct is an expression vector.

58. The method of claim 57, wherein the homologous or heterologous nucleic acid of the expression vector encodes a gene product and is operably linked to a suitable promoter sequence.

59. The method of claim 55, wherein the gene product is expressed in the cells.

60. The method of claim 52, wherein the therapeutic agent is an antibody.

61. The method of claim 52, wherein the therapeutic agent is an antibiotic.

62. The method of claim 38, wherein the active agent is selected from the group consisting of a hormone, a cytokine, a lymphokine, a growth factor, and a combination of any two or more of the foregoing compounds.

63. The method of claim 38, wherein the agent is mixed with a lipid.

64. The method of claim 38, wherein the agent is introduced encapsulated in a liposome or mixed with a charged lipid.

65. The method of claim 38, wherein the agent is in a liquid and the injector forces the liquid into the tissue as a conductive or essentially non-conductive liquid jet.

66. The method of claim 65, wherein the liquid jet acts as an electrode.

67. The method of claim 38, wherein the method further comprises applying iontophoresis to the tissue.

68. The method according to claim 38, wherein the agent is a proliferation-modulating agent.

69. The method according to claim 68, wherein the proliferation-modulating agent is selected from the group consisting of an antisense nucleic acid sequence, a ribozyme, a nucleic acid sequence, a triplex agent, and a combination of any two or more of the foregoing compounds.

70. The method according to claim 69, wherein introduction of the agent is performed to treat or prevent a cell-proliferative disorder or condition in the subject.

71. The method according to claim 38, wherein the agent comprises at least one antigenic epitope.

72. The method according to claim 71, wherein introduction of the agent is used to generates an immune response in the subject.

73. A method for administration of a biologically active agent into cells in an intramucosal region of tissue of a subject, said method comprising:
   a) using one or more needle-free injectors of an electroporation device to introduce said agent into said region in a form suitable for electrotransport, wherein said electroporation device comprises:
      i. at least one needle-free injector wherein at one of said needle-free injectors is configured to serve as a first electroporation electrode when positioned in contact with tissue of said subject;
      ii. a second electroporation electrode disposed in spaced relation to said first electroporation electrode; and
      iii. an energy source in electrical communication with said first and second electroporation electrodes to energize said first and second electroporation electrodes to effect electroporation; and
   b) using said electroporation device to generate an electric field sufficient to electroporate cells of said region, wherein said electroporating is conducted prior to, simultaneously with, and/or subsequently to introducing said agent into said region using at least one of said needle-free injectors to introduce the biologically active agent into said subject,
   whereby the combination of needle-free injection and electroporation is sufficient to introduce the agent-into cells in the intramucosal region.

74. The method of claim 73, wherein the electric field is generated by a square, rectangular, triangular, or exponential decay wave pulse.

75. The method of claim 74, wherein the pulse is of at least about 50V.

76. The method of claim 74, wherein the pulse is from about 100 μsec to about 100 msec.

77. The method of claim 74, wherein the pulse is monopolar or bipolar.

78. The method of claim 73, wherein administration with the needle-free injector is simultaneous with application of the electric field, and wherein the needle-free injector acts as an electrode.

79. The method of claim 73, wherein the electroporation device comprises at least two needle-free injectors, wherein the electric field is applied by contacting said tissues of said region with at least two of the needle-free injectors in spaced apart relation, with one of the injectors serving as a donor electrode and the other serving as a receptor electrode.

80. The method of claim 73, wherein application of the electric field and injection of the agent is substantially simultaneous.

81. The method of claim 73, wherein the agent is in the form of a conductive liquid.

82. The method of claim 81, wherein the agent is contained in a partially ionized solvent.

83. The method of claim 73, wherein the agent is contained within a controlled release vehicle.

84. The method of claim 73, wherein the method is performed in vivo.

85. The method of claim 73, wherein the subject is a mammal.

86. The method of claim 73, wherein the subject is a human.

87. The method of claim 73, wherein the agent is a therapeutic agent.

88. The method of claim 87, wherein the therapeutic agent is selected from the group consisting of a chemotherapeutic agent, a polynucleotide, a polypeptide, and a peptide.

89. The method of claim 87, wherein the therapeutic agent is a chemotherapeutic agent selected from the group consisting of bleomycin, neocarcinostatin, carboplatin, cisplatin, suramin, doxorubicin, mitomycin C, cisplatin, and a combination of any two or more of the foregoing compounds.

90. The method of claim 87, wherein the therapeutic agent is a nucleic acid construct encoding a homologous or heterologous gene product.

91. The method of claim 90, wherein the cells are transfected with the nucleic acid construct so that the gene product is expressed in the cells.

92. The method of claim 90, wherein the nucleic acid construct is an expression vector.

93. The method of claim 92, wherein the homologous or heterologous nucleic acid of the expression vector encodes a gene product and is operably linked to a suitable promoter sequence.

94. The method of claim 93, wherein the gene product is expressed in the cells.

95. The method of claim 87, wherein the therapeutic agent is an antibody.

96. The method of claim 87, wherein the therapeutic agent is an antibiotic.

97. The method of claim 87, wherein the agent is selected from the group consisting of a hormone, a cytokine, a lymphokine, a growth factor, and a combination of any two or more of the foregoing compounds.

98. The method of claim 87, wherein the agent is mixed with a lipid.

99. The method of claim 87, wherein the agent is introduced encapsulated in a liposome or mixed with a charged lipid.

100. The method of claim 87, wherein the agent is in a liquid and the injector forces the liquid into the tissue as a conductive or essentially non-conductive liquid jet.

101. The method of claim 100, wherein the liquid jet acts as an electrode.

102. The method of claim 87, wherein the method further comprises applying iontophoresis to the tissue.

103. The method according to claim 87, wherein the agent is a proliferation-modulating agent.

104. The method according to claim 87, wherein the proliferation-modulating agent is selected from the group consisting of an antisense nucleic acid sequence, a ribozyme, a nucleic acid sequence, a triplex agent, and a combination of any two or more of the foregoing compounds.

105. The method according to claim 87, wherein introduction of the active agent is in treatment or prevention of a cell-proliferative disorder or condition in a subject in need thereof.

106. The method according to claim 87, wherein the agent comprises at least one antigenic epitope.

107. The method according to claim 87, wherein introduction of the agent is used to generates an immune response in the subject.

* * * * *